United States Patent
Heltovics et al.

(10) Patent No.: US 7,208,464 B2
(45) Date of Patent: Apr. 24, 2007

(54) FRAGRANCE COMPOSITIONS

(75) Inventors: Gabor Heltovics, Budapest (HU); Lynette Anne Makins Holland, Herts (GB); Jill Maureen Mattila, Greensboro, NC (US); Jane Margaret Warwick, Willerby (GA)

(73) Assignee: The Procter & Gamble Company, Cincinnati, OH (US)

( * ) Notice: Subject to any disclaimer, the term of this patent is extended or adjusted under 35 U.S.C. 154(b) by 396 days.

(21) Appl. No.: 10/300,404

(22) Filed: Nov. 20, 2002

(65) Prior Publication Data

US 2003/0211125 A1 Nov. 13, 2003

Related U.S. Application Data

(63) Continuation of application No. PCT/US01/17734, filed on Jun. 1, 2001.

(30) Foreign Application Priority Data

Jun. 2, 2000 (GB) .................. 0013534.3
Nov. 3, 2000 (GB) .................. 0026969.6

(51) Int. Cl.
*A61Q 13/00* (2006.01)
(52) U.S. Cl. .................. 512/1; 510/101; 424/76.4
(58) Field of Classification Search .............. 512/1; 510/101; 424/76.4
See application file for complete search history.

(56) References Cited

U.S. PATENT DOCUMENTS

| 3,939,099 | A | | 2/1976 | Tusa et al. |
| 4,145,184 | A | * | 3/1979 | Brain et al. .................. 8/137 |
| 5,093,182 | A | | 3/1992 | Ross |
| 5,380,707 | A | | 1/1995 | Barr et al. |
| 6,013,618 | A | * | 1/2000 | Morelli et al. ............... 512/1 |
| 6,033,679 | A | | 3/2000 | Woo et al. |
| 6,110,449 | A | * | 8/2000 | Bacon et al. ................ 424/65 |
| 6,123,932 | A | * | 9/2000 | Guskey et al. .............. 424/65 |
| 6,458,754 | B1 | * | 10/2002 | Velazquez et al. .......... 510/441 |
| 6,544,945 | B1 | * | 4/2003 | Miracle et al. .............. 512/27 |

FOREIGN PATENT DOCUMENTS

| EP | 0 303461 | A | 2/1989 |
| JP | 58-052211 | A2 | 3/1983 |
| JP | A 6-287127 | | 10/1994 |
| JP | A 8-176587 | | 7/1996 |
| JP | A 8-183719 | | 7/1996 |
| JP | 5-230496 | A | 9/1996 |
| JP | A 10-120541 | | 5/1998 |
| WO | WO 98/07405 | A1 | 2/1998 |
| WO | WO 98/47477 | A1 | 10/1998 |
| WO | WO 98/47478 | A1 | 10/1998 |
| WO | WO 98/56341 | A1 | 12/1998 |
| WO | WO 99/43667 | A1 | 9/1999 |
| WO | WO 00/67714 | A1 | 11/2000 |
| WO | WO 01/93813 | A2 | 12/2001 |
| WO | WO 01/93815 | A2 | 12/2001 |

\* cited by examiner

*Primary Examiner*—Monique T. Cole
(74) *Attorney, Agent, or Firm*—Kenya T. Pierre; Andrew J. Hagerty; Tara M. Rosnell

(57) ABSTRACT

A composition comprising:
(a) a fragrance oil comprising:
(i) top note perfume raw material, or mixture of perfume raw materials, with a boiling point of less than, or equal to, about 250° C. at 1 atmosphere pressure;
(ii) middle or base note perfume raw material, or mixture of perfume raw materials, with a boiling point of greater than 250° C. at 1 atmosphere pressure;
(b) an entrapment material which is selected from the group consisting of polymers; capsules, microcapsules and nanocapsules; liposomes; pro-perfumes selected from more than 1 type of pro-chemistry; film formers; absorbents; cyclic oligosaccharides and mixtures thereof;
(c) greater than 50% volatile solvent;

wherein the weight ratio of the top note perfume raw materials to middle or base note perfume raw materials within the fragrance oil is in the range from about 1:20 to about 20:1.

The present invention provides compositions wherein the light, fresh, fruity, citrus, green or delicate floral top note fragrance character remains detectable for greater than about 2 hours, preferably greater than about 4 hours, more preferably greater than about 6 hours, after the composition has been applied to the substrate.

22 Claims, No Drawings

FRAGRANCE COMPOSITIONS

CROSS REFERENCE TO RELATED APPLICATIONS

This is a continuation of International Application PCT/US01/17734, filed Jun. 1, 2001.

FIELD OF THE INVENTION

The present invention relates to compositions, in particular cosmetic compositions, and more particularly fragrance compositions, which comprise a fragrance oil, an entrapment material and greater than 50% volatile solvent, wherein the fragrance oil comprises both "top note" and "middle and base note" perfume raw materials wherein the weight ratio of the two types of fragrance raw materials is in the range from about 1:20 to about 20:1. More particularly this invention relates to cosmetic compositions wherein the fragrance character of the "top note" perfume raw materials remains detectable on the substrate for at least 2 hours after application. Compositions of the present invention are suitable for application to a wide variety of substrates but particularly to the skin and hair.

BACKGROUND TO THE INVENTION

It has long been a feature of many types of compositions, including cosmetic compositions, that they comprise a fragrance oil for the purpose of delivering a pleasant smell. This can improve the overall consumer acceptance of the composition or mask unpleasant odours. In fact, it can be the sole purpose of some compositions to impart a pleasant odour to the skin, hair or other suitable substrate.

Fragrance oils used within cosmetic compositions usually comprise many different perfume raw materials. Each perfume raw material used differs from another by several important properties including individual character, volatility and the olfactory detection level (known as the odour detection threshold). By bearing in mind these different properties, and others, the perfume raw material can be blended to develop a fragrance oil with an overall specific character profile. It is usual that the character is designed to alter and develop with time as the different perfume raw materials evaporate from the substrate and are detected by the user. For example perfume raw materials which have a high volatility and low substantivity are commonly used to give an initial burst of characters such as light, fresh, fruity, citrus, green or delicate floral to the fragrance oil which are detected soon after application. Such materials are commonly referred to in the field of fragrances as "top notes". By way of a contrast, the less volatile, and more substantive, perfume raw materials are typically used to give characters such as musk, sweet, balsamic, spicy, woody or heavy floral to the fragrance oil which, although may also be detected soon after application, also last for longer. These materials are commonly referred to as "middle notes" or "base notes". Highly skilled perfumers are usually employed to carefully blend perfume raw materials so that the resultant fragrance oils have the desired overall fragrance character profile.

To date, the physical characteristics of the perfume raw materials themselves have limited the overall fragrance character profiles that can be created by perfumers. One such limitation is that it has only been possible to develop fragrance oils which impart a "top note" character for a short period of time. This is because the top note perfume raw materials are highly volatile and are therefore rapidly released from the substrate. As such, the longer lasting element of a fragrance character profile has been achieved by using middle and base notes which in turn restricts the achievable characters to musk, sweet, balsamic, spicy, woody or heavy floral and the like. Blending of higher levels of top note perfume raw materials to a fragrance oil does not improve the long lasting nature of the light, fresh, fruity, citrus, green, or delicate floral "top note" fragrance character, but instead could result in a stronger initial burst which again quickly evaporates and does not therefore last.

It is known that consumer preference for fragrance compositions is mostly driven by the initial "top note" character. It is therefore desirable to have a fragrance wherein the "top note" character is long lasting and perceived throughout use (ie after application of the composition to the substrate). It is also desirable to be able to create new to the world fragrance character profiles wherein one, or several, well recognised "top note" characters are maintained overtime such that a unique long lasting, "top, middle and base note" character is created. As such, it would be advantageous to be able to create a fragrance oil which will impart, in a new way, top note fragrance characteristics to a composition wherein the top note character is released from the composition over a substantial period of time, and, in particular, where the top note fragrance character remains detectable at least two hours after application.

In the past, many attempts have been made to delay the volatility profiles of fragrance oils within many types of compositions to extend the overall fragrance effect. For instance the fragrance oil may be formulated to include a higher proportion of perfume raw materials with a low volatility and which are therefore more substantive on the substrate. However, as discussed above, this restricts the fragrance character that can be achieved over time. Another approach has been to chemically, and reversibly, modify the perfume raw materials to a pro-perfume compound which is disclosed in patent applications WO 98/47477; WO 99/43667; WO 98/07405; WO 98/47478; all of which are incorporated herein by reference. The resultant pro-perfumes are not themselves volatile but, after the chemical modification is reversed, usually by hydrolysis upon application to the substrate, the perfume raw material is released and can then evaporate in the usual way. In these examples the release rate of the perfume raw materials is controlled by the reaction rate of the pro-perfume to perfume raw material transformation.

Further disclosures have discussed improving the overall longevity of a fragrance by delaying the evaporation of the fragrance oils. A wide variety of techniques have been disclosed among them encapsulation of the perfume raw materials for example within capsules (disclosed in JP-A-58/052211, EP-A-303,461), absorbing the materials to a surface for example by using carbon or zeolites (disclosed in U.S. Pat. No. 6,033,679), occluding the release of the perfume raw materials for example by the formation of a film (disclosed in U.S. Pat. No. 3,939,099) and complexing the perfume raw materials for example by using cyclic oligosaccharides. The prior art on this latter method includes JP-A-6/287127 and JP-A-8/176587 which disclose use of hydroxyalkylated cyclodextrins within cosmetic compositions to sustain the effect of the fragrance; and JP-A-8/183719 and JP-A-10/120541 which discloses a combination of cyclodextrin encapsulated fragrance and non encapsulated fragrance within a deodorant composition for prolonging the fragrance duration to at least 2 hours, all of which are incorporated herein by reference.

Whilst the compositions and disclosures of the prior art provide useful teachings for prolonging the overall fragrance character of a cosmetic composition the approaches still have limitations. The pro-perfume approach is limited by those chemical modifications that can suitably be made to the perfume raw materials. In addition, the prior art is restricted by pro chemistries used, or by the use of low levels of pro perfumes, thus preventing the development of a fragrance oil which exhibits a broad range of top note characters over time. On the other hand, entrapment materials, when used in the traditional way, interact with a broad range of perfume materials including top, middle and base notes prolonging the overall character of the whole fragrance. As such the prior art does not sufficiently teach how to preferentially delay evaporation of a large range of top note perfume materials within a single fragrance composition. In addition since, in general, entrapment such as that described suppresses the evaporation of only a relatively small amount of the perfume raw materials, the low level of delayed release is often not noticeable to the user. As such the prior art does not adequately teach how to provide a fragrance with long lasting and noticeable "top note" character.

Surprisingly, it has now been found that compositions, particularly cosmetic compositions, comprising a fragrance oil and a material which is able to delay the evaporation of the fragrance oil, wherein the fragrance oil is blended to comprise volatile "top notes" and residual "middle and base notes", wherein the weight ratio between these two types of notes is in the range from about 1:20 to about 20:1, and preferably in conjunction with a balance of perfume raw materials with a low odour detection threshold, can be used to create a long lasting fragrance character profile which has prolonged, and noticeable, "top note" characteristics. In addition, it has been found that within such fragrance oils, long lasting "top note" character can be combined with "middle and base note" characters to uniquely achieve a long lasting fragrance character profile with a broad spectrum of "top, middle and base notes" that it would not have been possible to develop using traditional perfumery.

While not wishing to be bound by theory, it is believed that when a composition according to the present invention is applied to a substrate an association exists between the perfume raw materials and the entrapment material such that the evaporation of the perfume raw materials is delayed. Over time, this association breaks down resulting in release of the perfume raw materials. Since the composition comprises a fragrance oil which has been developed with a given ratio of "top note" perfume raw materials to "middle and base note" perfume raw materials, the "top note" character continues to be experienced by the user over time. In addition, since the fragrance oil can preferably be developed with a balance of perfume raw materials with a low odour detection threshold, the user will experience a meaningful and novel fragrance character profile over time. This is because the perfume raw materials continue to remain detectable even though only a relatively small level is being released.

In addition, because the volatilisation rate of any given ingredient has, until now, been mainly related to its own boiling point, it has not been possible to obtain recurring and intermittent blooms (or pulses) of specific fragrance characters throughout the complete usage period. Surprisingly it has now been found that, once a substrate has been fragranced using a composition of the present invention, the fragrance can be refreshed over time, either naturally or deliberately, to release periodic and unexpected blooms of one or several fragrance characters. Whilst not wishing to be bound by theory, it is believed that this can be achieved by enhancing the natural decomposition rate of the fragrance oil entrapment material association for example by application of water, either naturally by breathing on the complex or by sweating, or artificially by spraying on a mist and the like. This "activation" results in the user experiencing a noticeable bloom of fragrance character. Surprisingly it has been found that it is possible to "activate" this complex, and thus generate fragrance blooms, several times during the wear. It is also believed that the negative consumer perception of becoming used to a scent can be minimised or prevented as a result of periodic "activation" resulting in an unexpected perceptible altering in the overall character of the fragrance.

It is an object of the present invention to provide compositions, particularly cosmetic compositions, which impart a long lasting and noticeable light, fresh, fruity, citrus, green or delicate floral "top note" fragrance character to the substrate on which they are applied. This, and other objects of this invention, will become apparent in light of the following disclosure.

SUMMARY OF THE INVENTION

The present invention relates to a composition comprising:
 (a) a fragrance oil comprising:
  (i) top note perfume raw material, or mixture of perfume raw materials, with a boiling point of less than, or equal to, about 250° C. at 1 atmosphere pressure;
  (ii) middle or base note perfume raw material, or mixture of perfume raw materials, with a boiling point of greater than 250° C. at 1 atmosphere pressure;
 (b) an entrapment material which is selected from the group consisting of polymers; capsules, microcapsules and nanocapsules; liposomes; pro-perfumes selected from more than 1 type of pro-chemistry; film formers; absorbents; cyclic oligosaccharides and mixtures thereof;
 (c) greater than 50% volatile solvent;

wherein the weight ratio of the top note perfume raw materials to middle or base note perfume raw materials within the fragrance oil is in the range from about 1:20 to about 20:1.

This invention further relates to methods of use for such compositions and the use of such compositions to delay the release of the volatile perfume raw materials from the substrate.

DETAILED DESCRIPTION OF THE INVENTION

All percentages and ratios used herein are by weight of the total composition and all measurements made are at 25° C., unless otherwise designated. Unless otherwise indicated all percentages, ratios and levels of ingredients referred to herein are based on the actual amount of the ingredient, and do not include solvent, fillers or other materials which may be combined with the ingredient in commercially available products.

All publications cited herein are hereby incorporated by reference in their entirety, unless otherwise indicated.

The term "dermatologically-acceptable," as used herein, means that the compositions, or components thereof, are suitable for use in contact with human skin without undue toxicity, incompatibility, instability, allergic response, and the like.

The term "safe and effective amount" as used herein means an amount of a compound, component, or composition sufficient to significantly induce a positive benefit, but low enough to avoid serious side effects, i.e. to provide a reasonable benefit to risk ratio, within the scope of sound medical judgement.

Active and other ingredients useful herein may be categorised or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The elements of these compositions are described in more detail below.

Fragrance Oil

Compositions of the present invention preferably comprise from about 0.01% to about 99%, preferably from about 0.25% to about 50%, more preferably from about 0.5% to about 40%, even more preferably from about 1% to about 25%, and most preferably from about 2.5% to about 25%, by weight, of the fragrance oil.

As used herein the term "fragrance oil" relates to the mixture of perfume raw materials that are used to impart an overall pleasant odour profile to a composition. As used herein the term "perfume raw material" relates to any chemical compound which is odiferous when in an unentrapped state, for example in the case of pro-perfumes, the perfume component is considered, for the purposes of this invention, to be a perfume raw material, and the pro-chemistry anchor is considered to be the entrapment material. In addition "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a programme called "CLOGP" which is available from Daylight Chemical Information Systems Inc., Irvine Calif., U.S.A. Octanol/water partition coefficients are described in more detail in U.S. Pat. No. 5,578,563.

Within the present invention, by mixing together several different perfume raw materials within the given "top note" to "middle and base note" weight ratio ranges a fragrance oil can be achieved which, when used in a composition, particularly a cosmetic composition, in conjunction with an entrapment material, is able to impart a particular long lasting character, which includes "top note" characters, to the composition in which it is used. The mixture of perfume raw materials used will be carefully chosen and blended to achieve a fragrance oil with the desired overall fragrance character profile.

The fragrance oil itself can comprise any perfume raw material suitable for use in the composition, particularly in cosmetic compositions. Overall the fragrance oil will most often be liquid at ambient temperatures and consist of a single individual perfume raw material. A wide variety of chemicals are known for fragrance uses, including materials such as aldehydes, ketones and esters. However, naturally occurring plant and animal oils and exudates comprising complex mixtures of various chemical components are also commonly known for use as fragrances. The individual perfume raw materials which comprise a known natural oil can be found by reference to Journals commonly used by those skilled in the art such as "Perfume and Flavourist" or "Journal of Essential Oil Research". In addition some perfume raw materials are supplied by the fragrance houses as mixtures in the form of proprietary speciality accords.

In order that fragrance oils can be developed with the appropriate character for the present invention the perfume raw materials have been classified based upon two key physical characteristics:

(i) boiling point (BP) measured at 1 atmosphere pressure. The boiling point of many fragrance materials are given in *Perfume and Flavor Chemicals (Aroma Chemicals)*, Steffen Arctander (1969). Perfume raw materials for use in the present invention are divided into volatile raw materials (which have a boiling point of less than, or equal to, about 250° C.) and residual raw materials (which have a boiling point of greater than about 250° C., preferably greater than about 275° C.). Volatile raw materials, for the purposes of this invention, are considered to be those that impart "top note" ie light, fresh, fruity, citrus, green or delicate floral characters to the fragrance oil and the like. Similarly the residual perfume raw materials are considered to be those that impart "middle or base note" ie musk, sweet, balsamic, spicy, woody or heavy floral characters to the fragrance oil and the like. All perfume raw materials will preferably have boiling points (BP) of about 500° C. or lower.

(ii) odour detection threshold which is defined as the lowest vapour concentration of that material which can be olfactorily detected. The odour detection threshold and some odour detection threshold values are discussed in e.g., "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978, both of said publications being incorporated by reference. Perfume raw materials for use in the present invention can be classified as those with a low odour detection threshold of less than 50 parts per billion, preferably less than 10 parts per billion and those with a high odour detection threshold which are detectable at greater than 50 parts per billion (values as determined from the reference above).

Since, in general, perfume raw materials refer to a single individual compound, their physical properties (such ClogP, boiling point, odour detection threshold) can be found by referencing the texts cited above. In the case that the perfume raw material is a natural oil, which comprises a mixture of several compounds, the physical properties of the complete oil should be taken as the weighted average of the individual components. In the case that the perfume raw material is a proprietary speciality accord the physical properties should be obtain from the Supplier.

In order to develop fragrance oils that are suitable for use in the present invention it is necessary that the weight ratio of volatile "top note" to residual "middle and base notes" perfume raw materials within the fragrance oil is in the range from about 1:20 to about 20:1, preferably from about 1:10 to about 10:1, more preferably from about 8:1 to about 1:2, most preferably from about 1.2:1 to about 1:1.2. It is preferred that the fragrance oil comprises about 5% or greater, more preferably about 5% to about 99%, even more preferably from about 5% to about 70%, further more preferably from about 10% to about 60%, and most preferably from about 25% to about 60%, by weight of fragrance oil, of volatile "top note" perfume raw materials ie with a boiling point of less than, or equal to, about 250° C. It is preferred that the fragrance oil also comprises from about 0.01% to about 95%, preferably from about 5% to about 85%, more preferably from about 10% to about 60%, by weight of fragrance oil, of the residual "middle and base note" perfume raw materials ie those with a boiling point of greater than about 250° C. In a very specific embodiment of this application the weight ratio of volatile "top note" to residual "middle and base notes" perfume raw materials within the fragrance oil is in the range from about 1:20 to about 1:19 and less than about 5%, by weight of the fragrance oil, of top note perfume raw materials. This embodiment allows for the fragrance character of a composition to be prolonged but is useful for preparing fragrance characters wherein the specific "top note" characters are less desirable, for example fragrance for use in male toiletries and the like.

Additionally, in order to develop fragrance oils with an appropriate character profile over time, it is preferred that within the fragrance oil a balance of perfume raw materials are used which have a low odour detection threshold. It is preferred for use herein that the "top note" perfume raw materials within the fragrance oil comprise 5% or greater, by weight of the "top note" perfume raw materials, of "top note" perfume raw materials which have an odour detection level of less than, or equal to, 50 parts per billion, preferably less than 10 parts per billion. In addition it is highly preferred that the "middle or base note" perfume raw materials within the fragrance oil comprise 10% or greater, more preferably 20% or greater and most preferably 50% or greater, by weight of the "middle or base note" raw materials, of "middle notes" or "base notes", or a mixture thereof, with an odour detection threshold of less than, or equal to, 50 parts per billion, preferably less than 10 parts per billion. Since materials with low odour detection levels can be detected when only very small levels are present, they are particularly useful for developing the long lasting character of the fragrance oil released over time from the entrapment material. Overall it is preferred that the whole fragrance oil comprise from about 5% to about 95%, preferably from about 20% to about 75%, more preferably from about 25% to about 50% and even more preferably from about 25% to about 40%, by weight of the fragrance oil, high odour impact perfume raw materials.

It is a further feature of the present invention that, the fragrance oil preferably comprising a balance of perfume raw materials with a low odour detection threshold, such that the compositions can comprise lower levels of fragrance oil than would traditionally be present. This can be advantageous for minimising skin sensitisation and also for reducing overall costs. As such, compositions of the present invention can preferably comprise from about 1% to about 15%, more preferably from about 1% to about 8%, by weight, of fragrance oil.

In general a broad range of suitable perfume raw materials can be found in U.S. Pat. Nos. 4,145,184, 4,209,417, 4,515,705, and 4,152,272. Non-limiting examples of perfume raw materials which are useful for blending to formulate fragrance oils for the present invention are given below. Any perfume raw materials, natural oils or proprietary speciality accords known to a person skilled in the art can be used within the present invention.

Volatile perfume raw materials ("top notes") useful in the present invention are selected from, but are not limited to, aldehydes with a relative molecular mass of less than or equal to about 200, esters with a relative molecular mass of less than or equal to about 225, terpenes with a relative molecular mass of less than or equal to about 200, alcohols with a relative molecular mass of less than or equal to about 200 ketones with a relative molecular mass of less than or equal to about 200, nitriles, pyrazines, and mixtures thereof.

Examples of volatile "top note" perfume raw materials having a boiling point of less than, or equal to, 250° C., with a low odour detection are selected from, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials having a boiling point of less than, or equal to, 250° C., which are generally known to have a low odour detection threshold include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, cis 1,3-oxathiane-2-methyl-4-propyl.

Other volatile "top note" perfume raw materials having a boiling point of less than, or equal to, 250° C., which are useful in the present invention, which have a high odour detection threshold, are selected from, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

Examples of residual "middle and base note" perfume raw materials having a boiling point of greater than 250° C., which have a low odour detection threshold are selected from, but are not limited to, ethyl methyl phenyl glycidate, ethyl vanillin, heliotropin, indol, methyl anthranilate, vanillin, amyl salicylate, coumarin. Further examples of residual perfume raw materials having a boiling point of greater than 250° C. which are generally known to have a low odour detection threshold include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde.

Other residual "middle and base note" perfume raw materials having a boiling point of greater than 250° C. which are useful in the present invention, but which have a high odour detection threshold, are selected from, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Entrapment Material

Compositions of the present invention comprise an entrapment material preferably at a level of from about 0.1% to about 95%, preferably from about 0.5% to about 50%, more preferably from about 1% to about 25% and even more preferably from about 2% to about 8%, by weight, of an entrapment material.

As defined herein an "entrapment material" is any material which, after application of the composition to a substrate, suppresses the volatility of the perfume raw materials within the fragrance oil thus delaying their evaporation. It is not necessary that the entrapment material forms an association with the perfume raw material within the composition itself, only that this association exists on the substrate after application of the composition. Non limiting examples of mechanisms by which the delay in evaporation may occur are by the entrapment material reversibly or irreversibly, physically or chemically associating with the perfume raw material through complexing, encapsulating, occluding, absorbing, binding, or otherwise adsorbing the perfume raw materials of the fragrance oil.

As defined herein "reversible entrapment" means that any entrapment material: perfume raw material association in which the association can be broken down so that the entrapment material and perfume raw materials are released from each other. As defined herein "irreversible entrapment" means that the entrapment material: perfume raw material association cannot be broken down. As defined herein "chemically associated" means that the entrapment material and perfume raw material are linked through a covalent, ionic, hydrogen or other type of chemical bond. As defined herein "physically associated" means that the entrapment material and perfume raw material are linked through a bond with a weaker force such as a Van der Waals force. Highly preferred is that, upon the substrate, the entrapment material and the perfume raw material form a reversible physical or chemical association.

As defined herein "to delay the evaporation of a perfume raw material" means to slow down or inhibit the evaporation rate of said perfume raw material from the substrate such that the fragrance "top note" character of the perfume raw material is detectable for at least 2 hours after application to the substrate.

Entrapment materials for use herein are selected from polymers; capsules, microcapsules and nanocapsules; liposomes; pro-perfumes selected from more than 1 type of pro-chemistry; film formers; absorbents; cyclic oligosaccharides and mixtures thereof. Preferred are pro-perfumes selected from more than 1 type of pro-chemistry, absorbents and cyclic oligosaccharides and mixtures thereof. Highly preferred are cyclic oligosaccharides.

Within the entrapment association it is preferred that the weight ratio of top note perfume raw material to entrapment material within the associated form is in the range from about 1:20 to about 20:1, more preferably in the range from about 1:10 to about 10:1, even more preferably in the range from about 1:10 to about 1:4.

Complexation Using for Example Cyclic Oligosaccharides

It is highly preferred for compositions of the present invention that the entrapment material reversibly, chemically and physically complexes the perfume raw materials.

Non limiting, and preferred, examples of entrapment materials that can act in this way are cyclic oligosaccharides, or mixtures of different cyclic oligosaccharides.

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to α, β and γ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof. Other cyclodextrin derivatives are disclosed in copending application U.S. Ser. No. 09/32192 (27$^{th}$ May 1999), all of which are incorporated herein by reference.

The substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$–$C_8$ alkyl or hydroxyalkyl groups or mixtures thereof, more preferred alkyl and hydroxyalkyl substituents are selected from $C_1$–$C_6$ alkyl or hydroxyalkyl groups or mixtures thereof, even more preferred alkyl and hydroxyalkyl substituents are selected from $C_1$–$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl substituents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. Most preferred examples of cyclic oligosaccharides for use herein are methyl-α-cyclodextrin and methyl-β-cyclodextrin. These are available from Wacker-Chemie GmbH Hanns-Seidel-Platz 4, Munchen, DE under the tradename Alpha W6 M and Beta W7 M respectively. Especially preferred is methyl-β-cyclodextrin.

Methods of modifying cyclic oligosaccharides are well known in the art. For example, see "*Methods of Selective Modifications of Cyclodextrins*" Chemical Reviews (1998) Vol. 98, No. 5, pp 1977–1996, Khan et al and U.S. Pat. No. 5,710,268.

In addition to preferred substituents themselves, it is also preferred that the cyclic oligosaccharides of the compositions used for the present invention have an average degree of substitution of at least 1.6, wherein the term "degree of substitution" means the average number of substituents per saccharide unit. Preferred cyclic oligosaccharides for use herein have an average degree of substitution of less than about 2.8. More preferably the cyclic oligosaccharides for use herein have an average degree of substitution of from about 1.7 to about 2.0. The average number of substituents can be determined using common Nuclear Magnetic Resonance techniques known in the art.

The cyclic oligosaccharides of the compositions used for the present invention are preferably soluble in both water and ethanol. As used herein "soluble" means at least about 0.1 g of solute dissolves in 100 ml of solvent, at 25° C. and 1 atm of pressure. Preferably the cyclic oligosaccharides for use herein have a solubility of at least about 1 g/100 ml, at 25° C. and 1 atm of pressure. Preferred is that cyclic oligosaccharides are only present at levels up to their solubility limits in a given composition at room temperature. A person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Encapsulation Using Capsules, Micro-capsules and Nano-capsules

Encapsulation of fragrances within capsules, micro-capsules or nanaocapsules which are broken down by environmental triggers can be used to reduce the volatility of fragrance oils by surrounding the oil by small droplets as a resistant wall. This may be either water sensitive or insensitive. In the first case the fragrance is released when the encapsulated particle is affected by moisture loss from the skin; while in the second case the capsule wall must be ruptured mechanically before the fragrance is released. Encapsulation techniques are well known in the art including DE 1,268,316; U.S. Pat. Nos. 3,539,465; 3,455,838.

Moisture sensitive capsules, micro-capsules and nanocapsules are preferably formed from, but not limited to, a polysaccharide polymer. Examples of suitable polymers are dextrins, especially low-viscosity dextrins including maltodextrins. A particularly preferred example of a low viscosity dextrin is one which, as a 50% dispersion in water has a viscosity at 25° C., using a Brookfield Viscometer fitted with an "A" type T-Bar rotating at 20 rpm in helical mode, of 330±20 mPa.s. This dextrin is known as Encapsul 855 and is available from National Starch and Chemicals Ltd. A further example of a polysaccharide that can be used to form the moisture sensitive capsules is gum acacia.

Time release micro-capsules are also suitable for use in compositions of the present invention for entrapping hydrophobic perfume raw materials. Such compositions comprise the perfume raw materials encapsulated in a wax or polymer matrix which in turn is coated with a compatible surfactant. The wax or polymers used to form the matrix have a melting point in the range from about 35° C. to about 120° C. at 1 atmosphere pressure. These are described in detail in EP-A-908,174.

Occlusion Using Film Formers

Film formers can also be used to reduce the volatility profile of perfume raw materials. When the fragrance is applied to a substrate, such as the skin, it is believed that film formers entrap the perfume oils during the evaporation of the volatile solvent thus hindering the release of the volatile material. Any film former which is compatible with the perfume raw materials may be used, preferably the film former will be soluble in water-ethanol mixture. Film former materials useful in this invention include, but are not limited to, ionic and non-ionic derivatives of water soluble polymers. Examples of suitable film forming materials are water soluble polymers containing a cationic moiety such as polyvinyl pyrrolidine and its derivatives having a molecular weight of 50,000 to 1,000,000. Other examples of ionic polymeric film forming materials are cationic cellulose derivatives sold under the trade names of Polymer JR (union Carbide), Klucel GM (hercules) and ethoxylated polyethyleneimine sold under the trade name PEI 600 (Dow). Examples of suitable cellulosic derivatives such as hydroxymethyl cellulose, hydroxypropyl methylcellulose and hydroxyethyl cellulose. Another examples of film formers is benzophenone.

Non limiting examples of film forming materials are given in U.S. Pat. No. 3,939,099.

Other Polymers

Additional non limiting examples of other polymer systems that can be used include water soluble anionic polymers e.g., polyacrylic acids and their water-soluble salts are useful in the present invention to delay the evaporation rate of certain amine-type odours. Preferred polyacrylic acids and their alkali metal salts have an average molecular weight of less than about 20,000, preferably less than 10,000, more preferably from about 500 to about 5,000. Polymers containing sulphonic acid groups, phosphoric acid groups, phosphonic acid groups and their water soluble salts, and their mixtures thereof, and mixtures with carboxylic acid and carboxylate groups, are also suitable.

Water soluble polymers containing both cationic and anionic functionalities are also suitable. Examples of these polymers are given in U.S. Pat. No. 4,909,986. Another example of water-soluble polymers containing both cationic and anionic functionalities is a copolymer of dimethyldiallyl ammonium chloride and acrylic acid, commercially available under the trade name Merquat 280® from Calgon.

Pro-Perfumes

Synthesising pro-perfumes or pro-fragrances from perfume raw materials can result in compounds which impart a delayed release mechanism to that specific perfume raw material. Pro-perfumes useful within the present invention include those selected from more than 1 type of pro-chemistry which ensures that a wide range of possible perfume raw materials can be used. This is consistent with the objective of providing unique fragrances with a broad spectrum of "top note" characters.

Within a pro-perfume the perfume raw material has been reacted with more than one type of chemical groups such as acetal, ketal, ester, hydrolysable inorganic-organic. As such, as defined within the present invention, the perfume raw material is considered to constitute part of the fragrance oil and the chemical groups to constitute part of the entrapment material. Pro-perfumes themselves are designed to be nonvolatile, or else have a very low volatility. However, once on the substrate, the perfume raw material is released from the pro-perfume. Once released the perfume raw material has its original characteristics. The perfume raw material may be released from the pro-perfume in a number of ways. For example, it may be released as a result of simple hydrolysis, or by shift in an equilibrium reaction or by a pH-change, or by enzymatic release. The fragrances herein can be relatively simple in their compositions, comprising a single chemical, or can comprise highly sophisticated complex mixtures of natural and synthetic chemical components, all chosen to provide any desired odour.

Non-limiting pro-perfumes suitable for use in the present application are described in WO 98/47477, WO 99/43667, WO 98/07405, WO 98/47478 and copending applications U.S Ser. No. 60/105380 (23rd Oct. 1998) and U.S. Ser. No. 60/130108 (20$^{th}$ Apr. 1999).

Absorption of Perfume Raw Material

When clarity of solution is not needed, odour absorbing materials such as zeolites and/or activated carbon can be used to modify the release rate of perfume raw materials.

A preferred class of zeolites is characterised as "intermediate" silicate/aluminate zeolites. The intermediate zeolites are characterised by $SiO_2/AlO_2$ molar ratios of less than about 10, preferably in the range from about 2 to about 10. The intermediate zeolites have an advantage over the "high" zeolites since they have an affinity for amine-type odours, they are more weight efficient for odour absorption since they have a larger surface area and they are more moisture tolerant and retain more of their odour absorbing capacity in water than the high zeolites. A wide variety of intermediate zeolites suitable for use herein are commercially available as Valfor® CP301-68, Valfor® 300-63, Valfor® CP300-35 and Valfor® 300-56 available from PQ Corporation, and the CBV100® series of zeolites from Conteka. Zeolite materials marketed under the trade name Abscents® and Smellrite® available from The Union Carbide Corporation and UOP are also preferred. These materials are typically available as a white powder in the 3–5 cm particle size range. Such materials are preferred over the intermediate zeolites for control of sulphur containing odours e.g., thiols, mercaptans.

Carbon materials suitable for use in the present invention are materials well known in commercial practice as absorbents for organic molecules and/or for air purification purposes. Often, such carbon material is referred to as "activated" carbon or "activated charcoal". Such carbon is available from commercial sources under trade names as; Calgon-Type CPG®; Type PCB®; Type SGL®; Type CAL®; and Type OL®.

Other odour absorbers suitable for use herein include silica molecular sieves, activated alumina, bentonite and kaolonite.

Volatile Solvent

Compositions of the present invention comprise greater than about 50%, preferably from about 55% to about 99.9%, more preferably from about 60% to about 95%, even more preferably from about 65% to about 75%, by weight, of a volatile solvent, or mixture of volatile solvents. Any volatile solvent suitable for use in the compositions can be used herein. The solvents for use herein are preferably organic volatile solvents.

As used herein, "volatile" refers to substances with a significant amount of vapour pressure under ambient conditions, as is understood by those in the art. The volatile solvents for use herein will preferably have a vapour pressure of about 2 kPa or more, more preferably about 6 kPa or more at 25° C. The volatile solvents for use herein will preferably have a boiling point under 1 atm, of less than about 150° C., more preferably less than about 100° C., even more preferably less than about 90° C., even more preferably still less than about 80° C.

Preferably the volatile solvents for use herein will be safe for use on a wide range of substrates, more preferably on human or animal skin or hair. Suitable volatile solvents include, but are not limited to, those found in the *CTFA International Cosmetic Ingredient Dictionary and Handbook*, 7$^{th}$ edition, volume 2 P1670–1672, edited by Wenninger and McEwen (The Cosmetic, Toiletry, and Fragrance Association, Inc., Washington, D.C., 1997). Conventionally used volatile solvents include $C_3$–$C_{14}$ saturated and unsaturated, straight or branched chain hydrocarbons such as cyclohexane, hexane, heptane, isooctane, isopentane, pentane, toluene, xylene; halogenated alkanes such as perfluorodecalin; ethers such as dimethyl ether, diethyl ether; straight or branched chain alcohols and diols such as methanol, ethanol, propanol, isopropanol, n-butyl alcohol, t-butyl alcohol, benzyl alcohol, butoxypropanol, butylene glycol, isopentyldiol; aldehydes and ketones such as acetone; volatile silicones such as cyclomethicones for example octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane; propellants, and mixtures thereof. Preferred volatile solvents are ethers such as dimethyl ether, diethyl ether; straight or branched chain alcohols and diols such as methanol, ethanol, propanol, isopropanol, n-butyl alcohol, t-butyl alcohol, benzyl alcohol, butoxypropanol, butylene glycol, isopentyldiol; volatile silicones such as cyclomethicones for example octamethyl cyclo tetrasiloxane and decamethyl cyclopentane siloxane; propellants, and mixtures thereof. More preferred for use herein are $C_1$–$C_4$ straight chain or branched chain alcohols for example methanol, ethanol, propanol, isopropanol and butanol and mixtures thereof, and most preferred for use herein is ethanol.

Balance of the Composition

The compositions herein are useful for use a fragrance component to a wide variety of different types of compositions including those such as cosmetic compositions, fragrance compositions for human or animal use, air freshener compositions, aromatherapy compositions, laundry and cleaning compositions, fragranced paper, cloth or other substrate type products and the like, in fact in any type of composition which comprises a fragrance. In all of these cases the compositions would comprise a variety of other optional ingredients which would render the compositions more acceptable or provide them with additional usage benefits. Such conventional optional ingredients are well-known to those skilled in the art and will vary greatly depending upon the field in which the compositions are to be used. Although compositions according to the second aspect of this invention comprise greater than 50% volatile solvent they should still be considered as being useful for inclusion in a wide variety of compositions with both cosmetic and non cosmetic benefits.

For cosmetic compositions in particular, the compositions can comprise any cosmetically acceptable ingredients such as those found in the *CTFA International Cosmetic Ingredient Dictionary and Handbook*, 7th edition, edited by Wenninger and McEwen, (The Cosmetic, Toiletry, and Fragrance Association, Inc., Washington, D.C., 1997). As used herein "cosmetically acceptable" means a material (e.g., compound or composition) which is suitable for use in contact with skin, hair or other suitable substrate as defined herein below. However that these ingredients are listed as useful for inclusion within a cosmetic composition does not preclude them from being incorporated into any other type of composition which comprises a fragrance formulated according to the present invention.

Nonvolatile Solvents

While the compositions of the present invention must comprise a volatile solvent they may also comprise "non-volatile" solvents. Suitable non-volatile solvents include, but are not limited to, benzyl benzoate, diethyl phthalate, isopropyl myristate, and mixtures thereof.

Molecular Wedges

When cyclic oligosaccharides are present in the compositions of the present invention, low molecular weight polyol molecular wedge having from about 2 to about 12 carbon atoms, preferably from about 2 to about 6 carbon atoms and at least one —OH functional group, preferably at least 2 —OH functional groups are preferably used herein for further prolonging the fragrance character of the composition. These polyols can further contain ether groups within the carbon chain. Suitable examples include ethylene glycol, propylene glycol, dipropylene glycol, 1,4-butanediol, 1,6-hexanediol and mixtures thereof. When present these polyols are present at a level of from about 0.01% to about 20%, preferably from about 0.1% to about 10%, and especially from about 0.5% to about 5% by weight of composition. It is preferred that the molar ratio of molecular wedge material to oligosaccharide is from 10:1 to 1:10, preferably 1:1 or greater, especially 1:1.

While not wishing to be limited by theory, the above mentioned molecular wedge molecules can form tertiary inclusion complexes with the complexed perfume material and the cyclic oligosaccharide. These small dipolar molcules can fit into the cavity of the cyclic oligosaccharide and anchor via their OH groups onto the outside rim of the cyclic oligosaccharide through hydrogen bonding. This enables the inclusion of all or parts of the fragrance material into the cavity of the cyclic oligosaccharide such that the stability of the formed tertiary complex is increased versus the complex formed by the fragrance material and cyclic oligosaccharide alone.

Water

The compositions of the present invention may also comprise water. If present, the water will preferably comprise from about 0.1% to about 40%, more preferably from about 1% to about 30%, even more preferably about 5% to about 20%, by weight, of total composition.

There are a number of other examples of additional ingredients that are suitable for inclusion into the present compositions. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hairhold polymers such as those described in WO-A-94/08557; salts in general, such as potassium acetate and sodium chloride and mixtures thereof. If present, these additional ingredients will preferably be present at a level of less than 10%, by weight, of total composition. More preferably these additional ingredients will be present at a level of less than 5%, by weight, of total composition.

Product Forms

The compositions for use in the present invention may take any form suitable for use, more preferably for cosmetic use. These include, but are not limited to, vapour sprays, aerosols, emulsions, lotions, liquids, creams, gels, sticks, ointments, pastes, mousses and cosmetics (e.g., semi-solid or liquid make-up, including foundations). Preferably the compositions for use in the present invention take the form of a vapour spray. Compositions of the present invention can be further added as an ingredient to other compositions in which they are compatible. As such they can be used within solid composition or applied substrates etc.

The compositions for use in the present invention will preferably comprise an acceptable carrier. The phrase "acceptable carrier", as used herein, means one or more compatible solid or liquid fillers, diluents, extenders and the like, which are acceptable as defined herein above. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilised in the present invention depends of the type of product desired and may comprise, but are not limited to, solutions, aerosols, emulsions (including oil-in-water or water-in-oil), gels, solids and liposomes.

Preparation of Composition

Compositions and fragrance oils for use in the present invention should be prepared according to procedures usually used in and that are well known and understood by those skilled in the art with materials of similar phase partitioning can be added in any order. The entrapment of the perfume raw materials can occur at any reasonable stage in the preparation of the overall composition. As such the fragrance oil can be prepared in its entirety, then entrapped with a suitable material before addition to the remainder of the composition. Alternatively the entrapment material can be added to the balance of the composition prior to addition of the complete fragrance oil. Finally it is possible to entrap any single perfume raw material, or group of raw materials, individually before either adding these to the balance of the fragrance oil or to the balance of the composition.

Methods of Use

The present invention preferably relates to compositions, particularly cosmetic compositions and more particularly fragrance compositions, which comprise a fragrance oil, in combination with an entrapment material, such that the fragrance profile of the top note perfume raw material, or mixture of raw materials, remains detectable for greater than about 2 hours, preferably greater than about 4 hours, more preferably greater than about 6 hours, after the composition has been applied to the substrate.

The composition itself is preferably used for providing fragrance to a suitable substrate. As used herein the term "suitable substrate" means any surface to which the present composition may be applied without an unduly adverse effect. This can include a wide range of substrates including human or animal skin or hair, paper, furnishings, materials, and can also include the air in a room. Preferred substrates are the skin or hair, especially the skin.

The preferred compositions of the present invention may be used in a conventional manner for fragrancing a suitable substrate. An effective amount of the composition, typically from about 1 μl to about 1000 μl, preferably from about 10 μl to about 250 μl, more preferably from about 25 μl to about 10 μl, is applied to the substrate. The composition may be applied by hand but is preferably applied utilising a vaporiser. Preferably, the composition is then left to dry.

Periodic blooming of the compositions of the present invention can be achieved by application, either naturally or artificially, of a material, such as water, which will drive the disassociation of the fragrance oil from the entrapment material. Such a bloom can be achieved naturally by seating, breathing on the fragranced substrate, rubbing the substrate and the like. In order to achieve such a bloom artificially it is necessary to use a refresher spray in conjunction with the compositions described herein. Such a refresher spray should comprise a material such as water which is capable of driving the break down of the fragrance oil entrapment material association. The refresher spray would be applied to the substrate, for example from an atomiser, whenever the boom was desired for example each hour after application of the fragrance to the substrate initially. Each time the refresher spray is applied it is expected that fragrance blooms would be achieved. It is expected that each fragrance bloom would last for less than about 30 minutes, preferably less than about 15 minutes, more preferably less than about 10 minutes and even more preferably less than about 5 minutes. Throughout wear a fragrance could be expected to be capable of blooming at least about 2 times or more, preferably about 4 times or more and more preferably about 6 times or more.

EXAMPLES

The following examples further illustrate the preferred embodiments within the scope of the present invention. These examples are given solely for the purposes of illustration and are not to be construed as limitations of the present invention as many variations of the invention are possible without departing from its spirit or scope. Unless otherwise indicated, all ingredients are expressed on a weight percentage of the active ingredient.

Fragrance Oil Examples I–VII
Examples I–VII are non limiting examples of the fragrance oil.

| Perfume Raw Material | I (%) | II (%) | III (%) | IV (%) | V (%) | VI (%) | VII (%) |
|---|---|---|---|---|---|---|---|
| damascone beta | 0.1 | 0.0 | 0.0 | 1.5 | 0.0 | 0.0 | 0.0 |
| allyl amyl glycolate | 0.1 | 0.0 | 0.0 | 0.0 | 0.0 | 0.3 | 0.3 |
| ionone beta | 3 | 2.5 | 0.0 | 0.0 | 0.0 | 0.0 | 0.0 |
| damascone alpha | 0.0 | 0.1 | 0.1 | 3 | 0.2 | 0.1 | 0.2 |
| methyl phenyl carbinyl acetate | 0.0 | 1.7 | 0.0 | 0.0 | 0.0 | 0.4 | 0.0 |
| cyclogalbanate[1] | 0.0 | 0.0 | 1.5 | 0.0 | 0.0 | 0.0 | 0.5 |
| methyl isobutenyl tetrahydro pyran | 0.0 | 0.0 | 0.3 | 0.0 | 0.0 | 0.0 | 0.1 |
| ethyl-2-methyl butyrate | 0.0 | 0.0 | 0.1 | 0.0 | 0.0 | 0.0 | 0.1 |
| fructone | 0.5 | 0.0 | 2.0 | 0.0 | 0.1 | 0.0 | 1 |
| flor acetate | 1 | 0.0 | 7.0 | 0.0 | 0.0 | 0.0 | 2 |
| ionone alpha | 0.5 | 0.0 | 3 | 3 | 0.3 | 0.0 | 1 |
| melonal | 0.0 | 0.0 | 0.0 | 1.5 | 0.2 | 0.0 | 0.0 |
| undecylenic aldehyde | 0.0 | 0.0 | 0.0 | 0.0 | 0.0 | 0.4 | 0.0 |
| Lemon Oil, Cold Pressed | to 100 | 5 | 0.0 | 0.0 | 0.0 | 0.5 | 0.0 |
| Bergamot Oil, Eco Essence | 25 | 0.0 | 0.0 | 14.5 | 0.0 | 1.5 | 0.0 |
| Cassis Base 345-L[2] | 1 | 0.0 | 0.0 | 30 | 3 | 1.0 | 0.0 |
| menthol | 0.5 | 0.0 | 0.0 | 0.0 | 0.0 | 0.0 | 0.0 |
| beta gamma hexenol | 0.5 | 1 | 0.6 | 0.0 | 0.0 | 0.0 | 0.0 |
| phenyl ethyl alcohol | 2 | 0.0 | 8 | 0.0 | 2.5 | 2.5 | 0.0 |
| phenoxy ethyl propionate | 0.0 | 0.0 | 0.0 | 0.0 | 0.5 | 0.0 | 0.0 |
| linalool | 8 | 5 | 0.0 | 0.0 | 0.0 | 1.5 | 0.0 |
| cis-3-hexenyl acetate | 0.0 | 0.2 | 0.0 | 0.0 | 0.0 | 0.0 | 0.0 |
| linalyl acetate | 0.0 | 5 | 0.0 | 0.0 | 0.0 | 1.2 | 0.0 |
| dihydro myrcenol | 0.0 | 2 | to 100 | 0.0 | 0.0 | 0.0 | 0.0 |
| citronellol | 0.0 | 10 | 0.0 | 0.0 | 0.0 | 1.5 | 0.0 |
| benzyl acetate | 0.0 | 6 | 0.0 | 0.0 | 0.0 | 4 | 0.0 |
| verdox | 0.0 | 0.0 | 7 | 0.0 | 0.0 | 0.0 | 0.0 |
| triplal | 0.0 | 0.0 | 0.6 | 0.0 | 0.0 | 0.2 | 0.0 |
| alpha terpineol | 0.0 | 0.0 | 0.0 | 0.0 | 0.0 | 1.2 | 0.0 |
| dihydro iso jasmonate | 3.5 | to 100 | 0.0 | 0.2 | 0.0 | 2 | 5 |
| cetalox[2] | 0.5 | 0.2 | 0.3 | 2.2 | 0.0 | 0.1 | 0.0 |
| bacdanol[3] | 0.1 | 0.0 | 1.5 | 0.0 | 0.0 | 0.0 | 1 |
| undecalactone | 1 | 2 | 2 | 0.0 | 0.0 | 10.3 | 1 |
| lyral[3] | 10 | 15 | 14 | 0.0 | 10 | 2 | 10 |
| florhydral[4] | 0.0 | 0.0 | 0.0 | 0.0 | 5 | 0.0 | 2 |
| cis-3-hexenyl salicylate | 0.0 | 2 | 0.0 | 0.0 | 0.0 | 1.2 | 2 |
| indol | 0.0 | 0.0 | 0.0 | 0.0 | 0.5 | 0.5 | 0.0 |
| ethyl vanillin | 0.0 | 0.8 | 0.7 | 1.3 | 0.0 | 0.0 | 0.0 |
| heliotropin | 0.0 | 0.0 | 0.0 | 0.0 | 0.5 | 0.0 | 1.6 |
| ebanol[4] | 0.0 | 2.0 | 0.0 | 0.0 | 0.0 | 0.0 | 0.0 |

Fragrance Oil Examples I–VII
Examples I–VII are non limiting examples of the fragrance oil.

| Perfume Raw Material | I (%) | II (%) | III (%) | IV (%) | V (%) | VI (%) | VII (%) |
|---|---|---|---|---|---|---|---|
| gamma decalactone | 0.0 | 0.0 | 0.0 | 4.5 | 0.4 | 0.0 | 0.0 |
| Prunella[2] | 0.0 | 0.0 | 0.0 | to 100 | 4 | 0.0 | 0.0 |
| lilial[4] | 0.0 | 0.0 | 0.0 | 0.7 | 0.0 | 15 | 10 |
| benzyl salicylate | 0.0 | 0.0 | 0.0 | 0.0 | to 100 | to 100 | 10 |
| oxocyclohexadecen-2-one | 0.0 | 8 | 10 | 1.5 | 10 | 0.2 | 15 |
| Roselea[3] | 0.0 | 0.0 | 0.0 | 0.6 | 0.0 | 0.0 | 5 |
| exaltolide | 2.5 | 8 | 12 | 0.0 | 12 | 0.4 | 8 |
| hexyl cinnamic aldehyde | 2.2 | 5 | 0.0 | 0.0 | 5 | 2 | 0.0 |
| zingerone[4] | 0.0 | 0.5 | 0.0 | 0.0 | 0.8 | 0.0 | 0.0 |
| methyl cedrylone | 0.0 | 3 | 0.0 | 0.0 | 15 | 0.0 | 4 |
| eugenol | 0.0 | 0.0 | 1.3 | 0.0 | 0.0 | 0.0 | 0.2 |
| sandela[4] | 0.0 | 0.0 | 0.0 | 0.0 | 0.0 | 10 | 5 |
| methyl dihydro jasmonate | 0.0 | 0.0 | 0.0 | 0.0 | 10 | 10 | to 100 |
| ionone gamma methyl | 0.0 | 0.0 | 0.0 | 0.0 | 0.0 | 10 | 0.0 |

[1] Dragoco Gerberding & Co AG, D-37601 Holzminden GERMANY
[2] Firmenich SA, 1 Route des Jeunes, CH-1211 Geneva 8 SWITZERLAND
[3] International Flavors & Fragrances 521 W. 57th St, New York, NY 10019 USA
[4] Givaudan-Roure 19-23 voie des Bans BP98, 95101 Argenteuil Cedex, FRANCE The perfume raw materials were mixed with stirring at room temperature.

Fragrance Compositions Examples VIII–XII

| | VIII (% wt) | IX (% wt) | X (% wt) | XI (% wt) | XII (% wt) |
|---|---|---|---|---|---|
| Fragrance (selected from examples I–VII) | 10 | 12.5 | 15 | 1.5 | 12 |
| Cyclic Oligosaccharide[5] | 2.5 | 5 | 10 | 2.5 | 0.0 |
| Pro-perfume I[6] | 0.0 | 0.0 | 0.0 | 0.0 | 0.4 |
| Pro-perfume II[7] | 0.0 | 0.0 | 0.0 | 0.0 | 0.4 |
| Ethanol | to 100 | to 100 | to 100 | to 100 | to 100 |
| Deionised Water | 15.75 | 13 | 11.5 | 15.8 | 0.0 |

[5] Beta W7 M available from Wacker-Chemie GmbH, Hanns-Seidel-Platz 4, Munchen, DE
[6] Pro-perfume comprising oxazolidine pro-melonal, Procter & Gamble, Cincinnati, Ohio
[7] Pro-perfume comprising beta-amino ketone pro-damascone, Procter & Gamble, Cincinnati, Ohio The cyclic oligosaccharide was dissolved in ethanol at room temperature with stirring. Then the fragrance and water were added with stirring.

Cosmetic Compositions Examples XIII–XV

| | XIII (% wt) | XIV (% wt) | XV (% wt) |
|---|---|---|---|
| Fragrance (selected from examples I–VII) | 3 | 2 | 3 |
| Cyclic Oligosaccharide[5] | 2 | 1.5 | 3 |
| Zinc phenolsulphonate | 2 | 1 | 2 |
| Dipropylene Glycol | 30.5 | 17 | 14.5 |
| Isopropyl myristate | 1.5 | 7 | 7 |
| Ethanol | to 100 | to 100 | to 100 |

[5] Beta W7 M available from Wacker-Chemie GmbH, Hanns-Seidel-Platz 4, Munchen, DE The zinc phenolsulphonate is stirred into the ethanol until fully dissolved. Then the dipropylene glycol is added with stirring. Next the isopropyl myristate, then the cyclic oligosaccharide and then the fragrance are all added with stirring. For an aerosol deodorant a propellant such as propane butane (CAP 40®) can be added to Examples XII–XIV according to standard industry practice.

When examples VIII–XV were applied to the substrate the light, fresh, fruity, citrus, green or delicate floral "top note" fragrance characters could still be determined at least two hours after application. By contrast, the same long lasting "top note" effect was not achieved when control compositions, comprising the same fragrance oil but without the entrapment material, were applied to a substrate.

What is claimed is:

1. A composition comprising:
   (a) a fragrance oil comprising:
      (i) one or more top note perfume raw materials, with a boiling point of less than, or equal to, about 250° C. at 1 atmosphere pressure;
      (ii) middle or base note perfume raw material, or mixture of perfume raw materials, with a boiling point of greater than 250° C. at 1 atmosphere pressure;

(b) an entrapment material which is not pre-associated with the fragrance oil prior to inclusion into the composition and which is selected from the group consisting of polymers; capsules, microcapsules and nanocapsules; liposomes; pro-perfumes selected from more than 1 type of pro-chemistry; film formers; absorbents; cyclic oligosaccharides and mixtures thereof;

(c) greater than about 50%, by weight, of a volatile solvent; and (d) from about 5% to about 20% water, by weight of the composition; wherein the weight ratio of the top note perfume raw materials to middle or base note perfume raw materials within the fragrance oil is in the range from about 1:20 to about 20:1.

2. A composition according to claim 1 wherein the weight ratio of the top note perfume raw materials to middle or base note perfume raw materials within the fragrance oil, is in the range of from about 1:10 to about 10:1.

3. A composition according to claim 1 wherein the composition comprises from about 0.01% to about 99%, by weight, of the fragrance oil.

4. A composition according to claim 1 wherein the top note perfume raw materials are selected from the group consisting of aldehydes with a relative molecular mass of less than or equal to about 200; eaters with a relative molecular mass of less than or equal to about 225; terpenes with a relative molecular mass of less than or equal to about 200; alcohols with a relative molecular mass of less than or equal to about 200 ketones with a relative molecular mass of less than or equal to about 200; nitriles; pyrazines; and mixtures thereof.

5. A composition according to claim 1 wherein the fragrance oil comprises from about 5% to about 99%. by weight of fragrance oil, of top note perfume raw materials.

6. A composition according to claim 1 wherein the fragrance oil comprises from about 0.01% to about 95%. by weight of fragrance oil, of the middle and base note perfume raw materials.

7. A composition according to claim 1 wherein the top note perfume raw materials of the flagrance oil comprise 5% or greater, by weight of the top note perfume raw materials, of top note perfume raw materials which have an odour detection threshold of less than, or equal to, 50 parts per billion.

8. A composition according to claim 1 wherein the middle or base note perfume raw materials of the fragrance oil comprise 10% or greater, by weight of the middle and base note perfume raw materials, of middle or base note perfume raw materials which have an odour detection threshold of less than, or equal to, 50 parts per billion.

9. A composition according to claim 1 wherein the entrapment material Is selected from the group consisting of pro-perfumes selected from more than 1 type of pro-chemistry; absorbents; cyclic oligosaccharides and mixtures thereof.

10. A composition according to claim 1 wherein the entrapment material is a cyclic oligosaccharide.

11. A composition according to claim 10 wherein the, cyclic oligosaccharide has six, seven or eight saccharide units and mixtures thereof.

12. A composition according to claim 10 wherein the cyclic oligosaccharide is substituted with a substituent selected from $C_1$–$C_8$ alkyl or hydroxyalkyl groups and mixtures thereof.

13. A composition comprising:
(a) a fragrance oil comprising:
  (i) one or more top note perfume raw materials, with a boiling point of less than, or equal to, about 250° C. at 1 atmosphere pressure;
  (ii) middle or base note perfume raw material, or mixture of perfume raw materials, with a boiling point of greater than 250° C. at 1 atmosphere pressure;
(b) an entrapment material which is not pre-associated with the fragrance oil prior to inclusion into the composition and which is selected from the group consisting of α-cyclodextrin, β-cyclodextrin, methyl-α-cyclodextrin, methyl-β-cyclodextrin, and mixtures thereof;
(c) greater than about 50% of a volatile solvent; and
(d) from about 5% to about 20% water, by weight of the composition; wherein the weight ratio of the top note perfume raw materials to middle or base note perfume raw materials within the fragrance oil is in the range from about 1:20 to about 20:1.

14. A composition according to claim 13 wherein the entrapment material is methyl-β-cyclodextrin.

15. A composition according to claim 1 which comprises from about 0.1% to about 95%, by weight, of said entrapment material.

16. A composition according to claim 1 wherein the volatile solvent has a boiling point, at 1 atmosphere pressure, of less than about 150° C.

17. A composition according to claim 1 wherein the volatile solvent is selected from the group consisting of ethers; straight or branched chain alcohols and diols; volatile silicones; propellants, and mixtures thereof.

18. A composition according to claim 1 wherein said composition comprises from about 55% to about 99.9%, by weight, of the volatile solvent.

19. A composition according to claim 1 wherein the composition is a cosmetic composition.

20. A method of fragrancing a substrate said method comprising the steps of:
  (i) applying a composition according to claim 1 to said substrate; and
  (ii) allowing said composition to dry.

21. A method for fragrancing a substrate, the method comprising the step of applying a composition to the substrate, the composition comprising:
(a) a fragrance oil comprising:
  (i) one or more top note perfume raw materials, with a boiling point of less than, or equal to, about 250° C. at 1 atmosphere pressure;
  (ii) middle or base note perfume raw material, or mixture of perfume raw materials, with a boiling point of greater than 250° C. at 1 atmosphere pressure;
(b) an entrapment material which is not pre-associated with the fragrance oil prior to inclusion into the composition and which is selected from the group consisting of polymers; capsules, microcapsules and nanocapsules; liposomes; pro-perfumes selected from more than 1 type of pro-chemistry; film formers; absorbents; cyclic oligosaccharides and mixtures thereof;
(c) greater than about 50%, by weight, of a volatile solvent; and wherein the weight ratio of the top note perfume raw materials to middle or base note perfume raw materials within the fragrance oil is in the range from about 1:20 to about 20:1;

whereupon after application to the substrate, at least some of the fragrance oil and the entrapment material form a reversible physical or chemical association.

22. The method of claim 21, wherein the entrapment material comprises cyclic oligosaccharides selected from the group consisting of α-cyclodextrin, β-cyclodextrin, methyl-α-cyclodextrin, methyl-β-cyclodextrin, and mixtures thereof.

* * * * *